United States Patent
Ben-Yakar et al.

(10) Patent No.: US 10,539,554 B2
(45) Date of Patent: Jan. 21, 2020

(54) HIGH-THROUGHPUT IMAGING PLATFORM

(71) Applicant: BOARD OF REGENTS, THE UNIVERSITY OF TEXAS SYSTEM, Austin, TX (US)

(72) Inventors: Adela Ben-Yakar, Austin, TX (US); Evan Hegarty, Austin, TX (US); Sudip Mondal, Austin, TX (US); Navid Ghorashian, Sunnyvale, CA (US); Sertan Kutal Gökçe, Austin, TX (US); Christopher Martin, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 230 days.

(21) Appl. No.: 15/522,116

(22) PCT Filed: Oct. 27, 2015

(86) PCT No.: PCT/US2015/057624
§ 371 (c)(1),
(2) Date: Apr. 26, 2017

(87) PCT Pub. No.: WO2016/069624
PCT Pub. Date: May 6, 2016

(65) Prior Publication Data
US 2017/0336394 A1    Nov. 23, 2017

Related U.S. Application Data

(60) Provisional application No. 62/068,822, filed on Oct. 27, 2014.

(51) Int. Cl.
*B01L 99/00* (2010.01)
*G01N 33/50* (2006.01)
(Continued)

(52) U.S. Cl.
CPC .... *G01N 33/5085* (2013.01); *B01L 3/502715* (2013.01); *B01L 3/502723* (2013.01);
(Continued)

(58) Field of Classification Search
None
See application file for complete search history.

(56) References Cited

U.S. PATENT DOCUMENTS 5,882,465 A * 3/1999 McReynolds ........... B29C 65/02
156/285
2005/0164158 A1    7/2005 Wang et al.
(Continued)

FOREIGN PATENT DOCUMENTS

| WO | 2011066497 A2 | 6/2011 |
| WO | 2013119765 A1 | 8/2013 |
| WO | 2014138203 A2 | 9/2014 |

OTHER PUBLICATIONS

Office Action in EP Application No. 15854886.7, dated Jan. 21, 2019.
(Continued)

*Primary Examiner* — Paul S Hyun
(74) *Attorney, Agent, or Firm* — Meunier Carlin & Curfman LLC

(57) ABSTRACT

A microfluidic device capable of trapping contents in a manner suitable for high-throughput imaging is described herein. The microfluidic device may include one or more trapping devices, with each trapping device having a plurality of trapping channels. The trapping channels may be configured to receive contents via an inlet channel that connects a sample reservoir to the trapping channels via fluid communication. The trapping channels are shaped such that contents within the trapping channels are positioned for optimal imaging purposes. The trapping channels are also (Continued)

connect to at least one exit channel via fluid communication. The fluid, and contents within the fluid, may be controlled via hydraulic pressure.

10 Claims, 9 Drawing Sheets

(51) Int. Cl.
  *G01N 21/64*    (2006.01)
  *G01N 21/05*    (2006.01)
  *B01L 3/00*    (2006.01)
  *G01N 35/00*    (2006.01)
  *G06K 9/00*    (2006.01)

(52) U.S. Cl.
  CPC ... *B01L 3/502746* (2013.01); *B01L 3/502761* (2013.01); *G01N 21/05* (2013.01); *G01N 21/6458* (2013.01); *G01N 33/502* (2013.01); *G01N 35/00029* (2013.01); *G01N 35/00871* (2013.01); *G06K 9/0014* (2013.01); *G06K 9/00134* (2013.01); *B01L 2300/023* (2013.01); *B01L 2300/0654* (2013.01); *B01L 2300/0864* (2013.01); *B01L 2300/14* (2013.01); *G01N 2021/6482* (2013.01); *G01N 2035/00148* (2013.01); *G01N 2201/12* (2013.01)

(56) References Cited

U.S. PATENT DOCUMENTS

| | | |
|---|---|---|
| 2007/0243523 A1 | 10/2007 | Ionescu-Zanetti et al. |
| 2009/0010388 A1* | 1/2009 | Stahly ............... G01N 21/253 378/79 |
| 2012/0241643 A1 | 9/2012 | Palmer et al. |
| 2014/0051174 A1 | 2/2014 | Burke et al. |
| 2014/0247971 A1 | 9/2014 | Bharadwaj et al. |

OTHER PUBLICATIONS

International Search Report and Written Opinion in International Application No. PCT/US15/57624, dated Feb. 18, 2016.
International Preliminary Report on Patentability in International Application No. PCT/US15/57624, dated May 11, 2017.
Extended European Search Report issued in EP Application No. 15854886.7, dated Jun. 6, 2018.
Nilsson, et al., "Review of cell and particle trapping in microfluidic systems", Analytica Chimica Acta 649 2009, 141-157.
Hulme, et al., "A microfabricated array of clamps for immobilizing and imaging C. elegans", Lab on a Chio, 7(11) 2007, p. 1515.
Hegarty, "Autimated parallel immobilization microfluidic platforms for high-throughput neuronal degeneration studies with C. elegans", Master Thesis, Dec. 1, 2014, 73 pages.
Partial Supplementary European Search Report issued for European Application No. 15854886.7, dated Mar. 5, 2018, 24 pages.
Office Action in JP Application No. 2017-522589, dated Aug. 27, 2019 (machine translation and summary from JP attorney included).
Communication Pursuant to Article 94(3) EPC, issued in EP15854886.7, dated Sep. 13, 2019.
Australian Examination Report issued in AU2015339464 dated Oct. 22, 2019.

* cited by examiner

STITCHED IMAGE OF 40 CHANNELS (WELL# C03)

CROP INDIVIDUAL ANIMAL

THRESHOLD AND FILTER IMAGE

HIGH-THROUGHPUT IMAGING PLATFORM

CROSS-REFERENCE TO RELATED APPLICATIONS

This application claims priority to and benefit of U.S. Provisional Patent Application Ser. No. 62/068,822 filed Oct. 27, 2014, which is fully incorporated by reference herein and made a part hereof.

STATEMENT REGARDING FEDERALLY SPONSORED RESEARCH OR DEVELOPMENT

This invention was made with Government Support under Grant Nos. #R01AG041135 and #R01NS060129 awarded by the National Institutes of Health. The Government has certain rights in the invention.

BACKGROUND

Drug discoveries require methodologies to screen new compounds in small quantities using model systems in a high-throughput manner. Screening compounds in model systems are necessary to obtain new hits before the compounds are taken for clinical or human trials. The two types of model systems are in vitro (performed with cells or biological molecules outside their normal biological context) and in vivo (performed on whole, living organisms) model systems. Whole organism in vivo models are far better than the 2D/3D in vitro systems that use cell lines, accounting for more factors and providing more accurate results.

Traditionally, high-throughput drug screens are based on in vitro cell cultures which do not delineate all the aspect of in vivo testing such as drug absorption, circulation, metabolism, excretion, and toxicity as found in humans. Use of in vitro model in drug discoveries has encountered with poor hit-to-lead rates and clinical translation. On the other hand, traditional in vivo testing models have been either low-throughput or low resolution, hindering the testing process.

Typically, in vivo models are conducted on basic organisms such as *C. elegans, C. brigsae*, and plenaria. The *C. elegans* is particularly well suited to in vivo models due to its short life span, well characterized genetics, simple neuronal circuit, small number of cellular architecture, and amenable worm body throughout its development. The *C. elegans* genome share approximately 65% homology with human disease genes and has been an attractive platform for elucidating disease pathways. Because of its faster life cycle and smaller genome size, *C. elegans* provides a useful tool for genetic manipulation. New disease models have been demonstrated using *C. elegans* for neurological diseases, genetic disorder, cancer, and developmental disorder etc.

The typical testing methods for worms such as *C. elegans* includes placing the worms in the wells of a multi-well plate and analyzing them using anesthetic solution. However, the worms in the wells are not aligned or organized properly using this method. For example, in high density fluid the worms can settle at the bottom of the well and stack up on top of each other. On the other hand, in low density fluid the worms are better isolated but require more imaging data in order to produce sufficient data for statistical analysis. In light of the drawbacks of current methods, there exists a need for a high-throughput imaging system for accurate, high quality, and high speed in vivo screening of organisms such as *C. elegans*.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The following detailed description will be better understood when read in conjunction with the appended drawings, in which there is shown one or more of the multiple embodiments of the present invention. It should be understood, however, that the various embodiments of the present invention are not limited to the precise arrangements and instrumentalities shown in the drawings.

DETAILED DESCRIPTION

A microfluidic device capable of trapping contents in a manner suitable for high-throughput imaging is described herein. The microfluidic device may include one or more trapping devices, while each trapping device may have a plurality of trapping channels. The trapping channels may be configured to receive contents via an inlet channel that connects a sample reservoir to the trapping channels via fluid communication. The trapping channels are shaped such that contents within the trapping channels are positioned for optimal imaging purposes. The trapping channels are also connected to at least one exit channel via fluid communication. The fluid, and contents within the fluid, may be controlled via hydraulic pressure.

Figure 1:
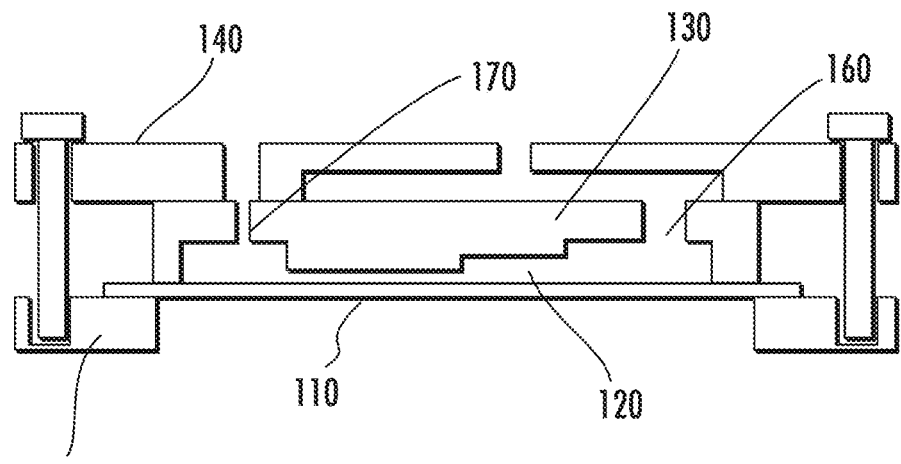
FIG. 1 is a cross-sectional view of an example embodiment of a microfluidic device.

An example microfluidic device is shown in FIG. 1. The device shown in FIG. 1 includes a substrate 110 upon which a trapping channel 120 is built. Substrate 110 may comprise any suitable material for building a trapping channel upon. For example, substrate 110 may be glass, metal, plastic, or any other suitable material. Trapping channel 120 may be formed via a void in material 130. Material 130 may include any suitable material for forming trapping channel 120, such as, for example, polydimethylsiloxane. Any other material capable of being formed into an appropriate shape may also be used. Material 130 may also include an inlet 160 and an exit 170 to allow fluid to flow through trapping channel 120.

FIG. 1 also shows top gasket 140 and bottom gasket 150, which may be incorporated into the microfluidic device in order to influence fluid dynamics of the fluid used with the device. For example, top gasket 140 may include channels for coupling trapping channel 120 to other fluid pathways. Top gasket 140 may also include a passageway for releasing air or other gasses trapped within the fluid in the system. Bottom gasket 150 may be used to seal the bottom portion of the device and prevent fluid leaks while maintaining appropriate pressure levels. Screws 180 may be utilized to secure the substrate 110, trapping channel 120, material 130, top gasket 140, and/or bottom gasket 150.

Figure 2:
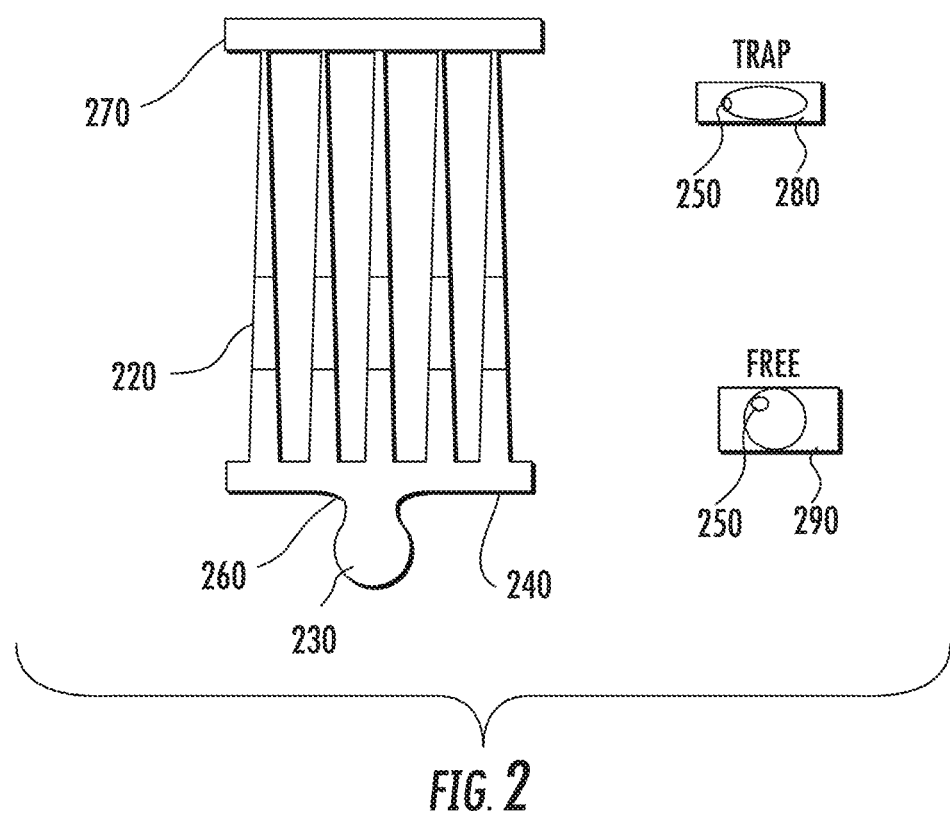
FIG. 2 is an example embodiment of a trapping device having multiple trapping channels.

FIG. 2 shows an example embodiment of a trapping device having multiple trapping channels. In this embodiment, the trapping device includes five trapping channels 220. The trapping channels 220 may receive fluid via inlet channel 260, which in turn may receive fluid via reservoir 230. Reservoir 230 may be filled with fluid via a well (not shown) or any other suitable method. In the example embodiment of FIG. 2, the fluid contains subjects 240. Subjects 240 may be any suitable subject for testing, including animals. For example, subjects 240 may be *C. elegans*, a small worm commonly used for testing pharmaceutical products in vivo. Trapping channels 220 may also be connected to exit channel 270 via fluid communication, such that the imaged subjects 240 and associated fluid exits through exit channel 270. The term "fluid communication" is used broadly to mean that fluid flow is possible between two locations. Fluid communication does not require consistent fluid flow, but rather the ability to transport fluid from a first location to another.

FIG. 2 also includes cross-sectional views of a trapping channel 220 at different points along its length. Cross section 290, labeled "free," is a cross-sectional view of trapping channel 220 at a first section of the channel. Cross section 280, labeled "trap," is a cross-sectional view of trapping channel 220 at a second section of the channel. A "section" of a channel may comprise a measurable length of the channel, or may comprise an infinitesimal portion of the channel. A comparison of these two cross sections makes it clear that cross section 280 is smaller in at least one dimension relative to cross section 290. In this embodiment, the cross section size of cross section 280 may cause the point of interest 250 to align in a particular way.

In an example embodiment, point of interest 250 represents the ventral side of subject 240, particularly a *C. elegans* organism. The shape of trapping channel 220 may be varied to orient point of interest 250 in a particular direction. In this manner each trapping channel 220 may trap and orient subjects 240 in similar orientations. This orientation aids in image capture, as the image can be captured from the ideal direction in a repeatable manner. Point of interest 250 may represent different portions of the *C. elegans* or may relate to a different organism entirely. While *C. elegans* are discussed herein, the subject matter of this application is not limited to this particular type of organism.

Trapping channel 220 may have a height and width, measured relative to a support surface such as substrate 110 in FIG. 1. In one embodiment, trapping channel 220 is aligned such that its length is parallel to the surface of the substrate. The "height" of trapping channel 220 can therefore be measured in a direction perpendicular to the surface of the substrate. The "width" of trapping channel 220 can be measured in a direction parallel to the surface of the substrate but perpendicular to the axial direction along the length of trapping channel 220.

In one embodiment, the height of trapping channel 220 is varied along at a plurality of locations along the length of the channel. For example, the heights of at least two of the sections of trapping channel 220 may differ from one another. In another example, the height of trapping channel 220 is varied continuously along at least a portion of the length of the channel. In one example, the variations in height are provided such that the height of trapping channel 220 decreases in the direction of flow—i.e from the inlet channel side to the exit channel side of the trapping channels.

The particular dimensions of the microfluidic device can vary based on implementation. In one example embodiment, however, inlet channel 260 comprises a height of about 1 µm to about 500 µm and a width of about 1 µm to about 750 µm. In another example embodiment, the length of trapping channel is about 200 µm to about 6 mm.

Figure 3:
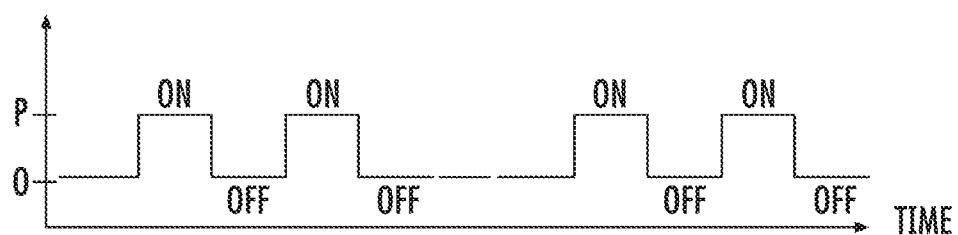
FIG. 3 is a graph showing pressure cycles for an example embodiment.

In order to control the flow of fluid through the microfluidic device, pressure regulation may be used. Any suitable method for controlling pressure may be used. FIG. 3 shows a graph of an example pressure regulation cycle that may be used. The graph in FIG. 3 shows that the pressure is cycled between "ON" and "OFF" states in a cyclical manner. Any appropriate pressure levels may be used, and should be matched to the size of the microfluidic device, trapping channels, and subjects being tested. In one example embodiment, the pressure is cycled between about 0 and 30 psi. Similarly, the time period for the cycles may be tailored to the particular device. In one example embodiment, each pressure cycle is maintained for a time period of 0 to 600 seconds.

Figure 4:
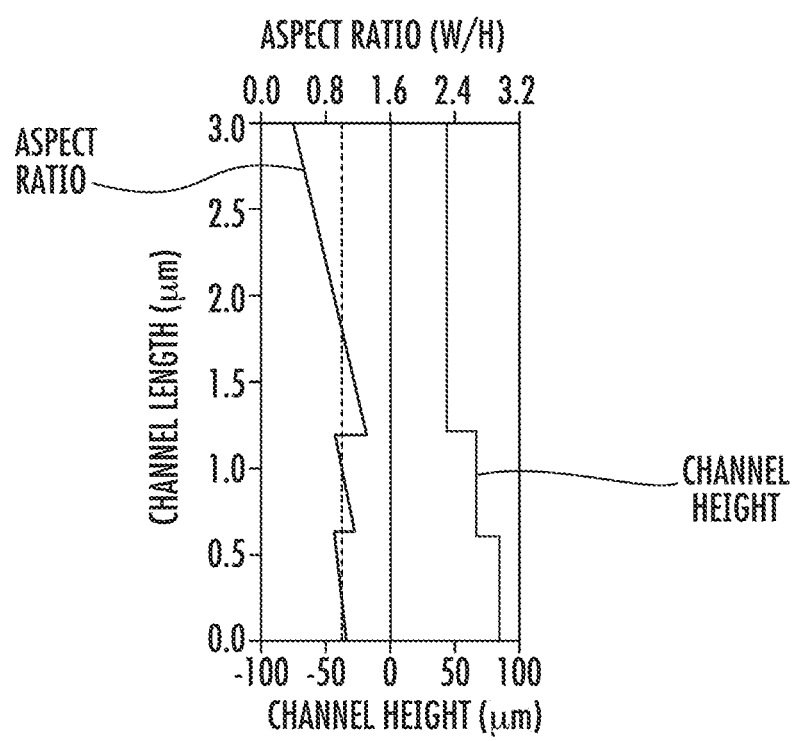
FIG. 4 is a graph for an example embodiment illustrating aspect ratio versus channel length and channel height versus channel length.

FIG. 4 is a graph for an example embodiment illustrating aspect ratio versus channel length and channel height versus channel length. The axis along the left side of the graph is channel length, measures in millimeters, and ranges from 0.0 to 3.0. Along the top of the graph is aspect ratio, measured as width divided by height. The aspect ratio is illustrated by the line that roughly follows the dotted line. In this embodiment, the aspect ratio varies from about 0.4 to about 1.2. In some embodiments, the aspect ratio remains within a range of about 0.2 to about 2.0. Along the bottom of the graph is channel height, measured in micrometers. The line on the right represents channel height, and ranged from about 50 to about 100 µm in this particular embodiment. In other embodiments, the height may range from about 1 µm to about 500 µm along the length of the trapping channel.

Figure 5:
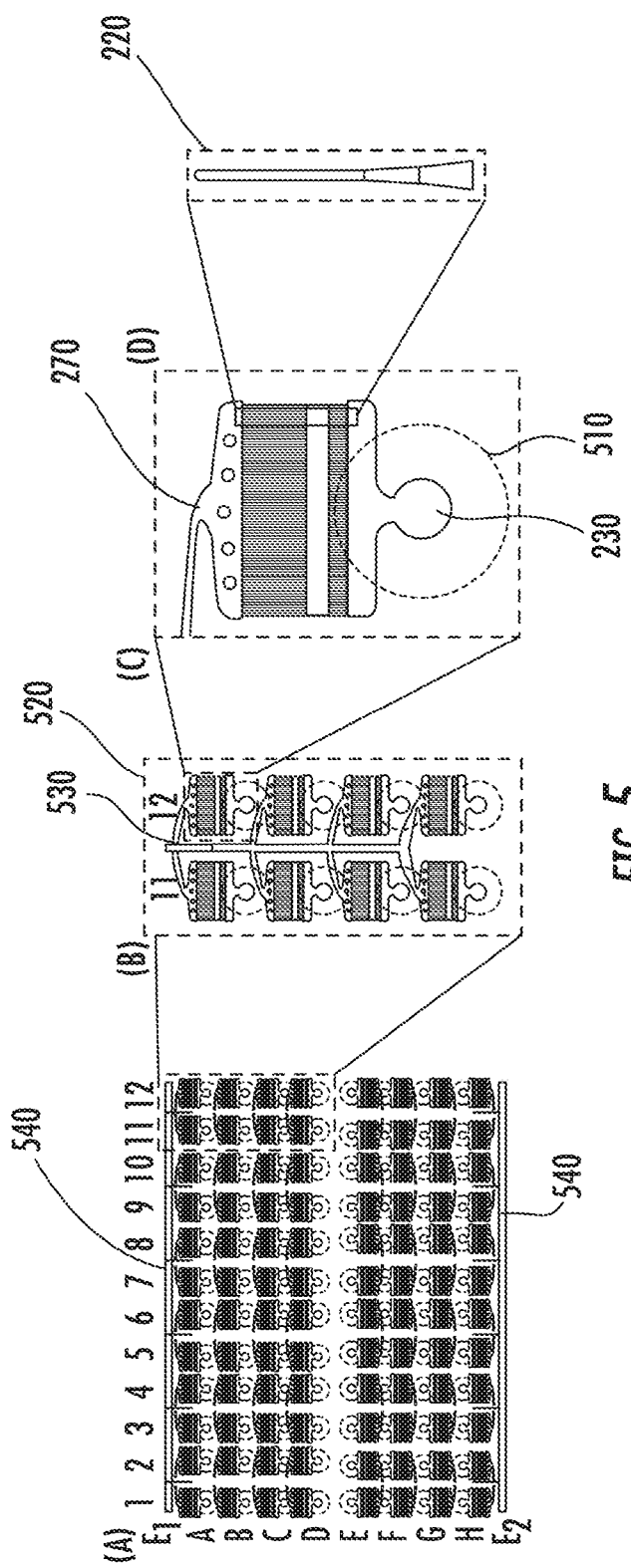
FIG. 5 is an example embodiment of a microfluidic device having a plurality of trapping devices.

FIG. 5 is an example embodiment of a microfluidic device having a plurality of trapping devices. In this example embodiment, the microfluidic device labeled as "(A)" contains 96 individual trapping devices. In other embodiments, however, any number of trapping devices may be used. A subset 520 of trapping devices is labeled as "(B)." The subset 520 of trapping devices includes an intermediate exit channel 530. Each of the eight trapping devices in subset 520 have an individual exit channel in fluid communication with intermediate exit channel 530. In one embodiment, the trapping devices have different size exit channels in order to equalize pressure among the various trapping devices. For example, the trapping devices labeled D11 and D12 in subset 520 have larger exit channels than the trapping devices labeled A11 and A12. In this embodiment, A11 and A12 are closer to the exit point of intermediate exit channel 530, and therefore smaller exit channels can suffice. On the other hand, D11 and D12 are farther from the exit point of intermediate exit channel 530, and therefore larger exit channels are necessary.

The intermediate exit channels 530 from each subset of trapping devices may join in fluid communication a final exit channel 540. The microfluidic device labeled (A) in FIG. 5 shows two final exit channels 540 on opposite sides of the device. The final exit channels 540 may be formed by a gasket surrounding the microfluidic device. The exit channels 270, intermediate exit channels 530, and final exit channels 540 may be configured such that the hydraulic resistance experience by each trapping device is similar across all applicable trapping devices.

In order to provide the fluid and subjects for testing to the microfluidic device, the fluid and subjects may be deposited in the reservoirs 230 of one or more trapping devices. In an exemplary embodiment, wells 510 are used to control the deposition of this subject matter to the reservoirs 230. In FIG. 5, the trapping device labeled "(C)" shows a dotted line for well 510 because the well is positioned above the plane of the trapping device. Well 510 may be a funnel, syringe, hose, tube, or any other device for providing fluid and subjects for testing. In one embodiment, well 510 is a substantially frustoconical shape with the smaller end of the shape proximate the reservoir 230.

The microfluidic device described in various example embodiments above may be incorporated into a high-throughput imaging system. In one example embodiment, the imaging system includes a microfluidic device, a pressure device connected to the microfluidic device via a fluidic connection, a microscope with a camera and a motorized platform, and a processor. In one embodiment, the motorized platform is configured to support the microfluidic device such that any changes in the location of the motorized platform also moves the microfluidic device. In other embodiments, the motorized platform may move the camera or other imaging equipment used in conjunction with the camera. Regardless of the implementation, the motorized platform may be capable of moving in three dimensions.

In one embodiment, the process comprises computer-readable instructions for applying hydraulic pressure to the microfluidic device, moving the motorized platform such that the camera captures the contents of the microfluidic device, capturing the contents of the microfluidic device as image files, and saving and storing the image files to a storage device.

The imaging system may also be capable of calculating and adjusting for various imperfections in the system. For example, the system may be capable of calculating offsets in a focusing plane of the contents in the trapping devices. These offsets may be caused by, for example, imperfections in the manufacturing process of the devices. Similarly, the system may be able to calculate a curvature of the substrate used for the microfluidic device. The substrate may undergo curving due to the hydraulic pressure used within the trapping devices. The system can therefore measure or calculate the curvature based on the pressure and/or measurements at locations of the substrate. This may include obtaining x, y, and z coordinates of a plurality of predetermined locations of the microfluidic device. The system may then move the motorized platform and/or adjust the camera settings to compensate for the factors described above.

An image analyzer may also be used in conjunction with the imaging system. In one embodiment, the imager analyzer receives stored images for analysis. The analyzer can identify the trapping channels and the desired contents of the trapping channels, and crop the image to remove the portions of the trapping channels that do not have the desired contents. The analyzer is also capable of comparing a plurality of images of the desired contents at different focal planes. The images at different focal planes may be considered different images in the image stack, or z-stack. The analyzer can select the most desirable image in the stack and display a version of that image on a graphical user interface.

In one embodiment, the display settings of the images on the graphical user interface can be adjusted in real time to aid in scoring phenotypes. In another embodiment, a particle size filter can be used to remove all foreign particles in the area of interest on the graphical user interface. In some embodiments, the image analyzer is automated and can select focal planes and score phenotypes automatically.

Figure 6:
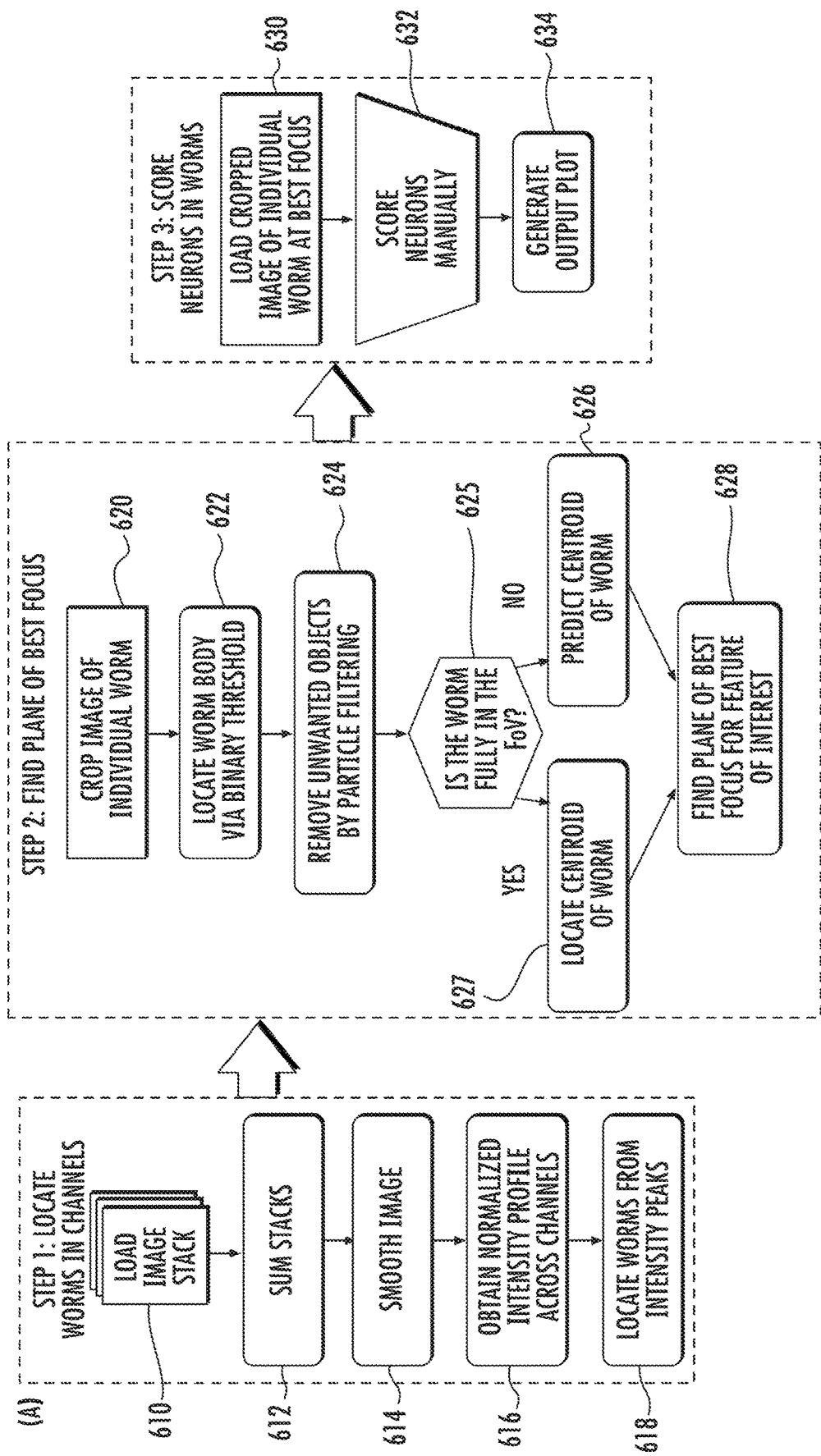
FIG. 6 shows flow charts for three steps in the process of analyzing images in an example embodiment.

FIG. 6 discloses flow charts describing an example embodiment of an image analysis for neuronal health assessment of *C. elegans* organisms. Each flow chart describes a particular task, such as locating the worms, finding the plane of best focus, and scoring neurons in the worms.

With respect to locating worms in the channels, block 610 initiates the process of loading an image stack. At block 612 the stacks are summed. At block 614 the images are smoothed according to a smoothing process. At block 616 the system obtains a normalized intensity profile across channels. And at block 618 the worms are located from intensity peaks. Next, at block 620 the images of individual worms are cropped and at block 22 the worm body is located via a binary threshold. At block 624 unwanted objects are removed via particle filtering. Block 625 queries whether the worm is fully in the field of vision. If not, then at block 626 the centroid of the worm is predicted. If so, then the centroid of the worm is located at block 627. At block 628, the plane of best focus for the feature of interest is located. Finally, the neurons are scored for the worm. At block 630 the cropped, filtered images are loaded. At block 632 the neurons of interest are manually scored—although in other embodiments this step is completed automatically. At block 634 an output plot is generated and may be displayed on a graphical user interface.

Figure 7:
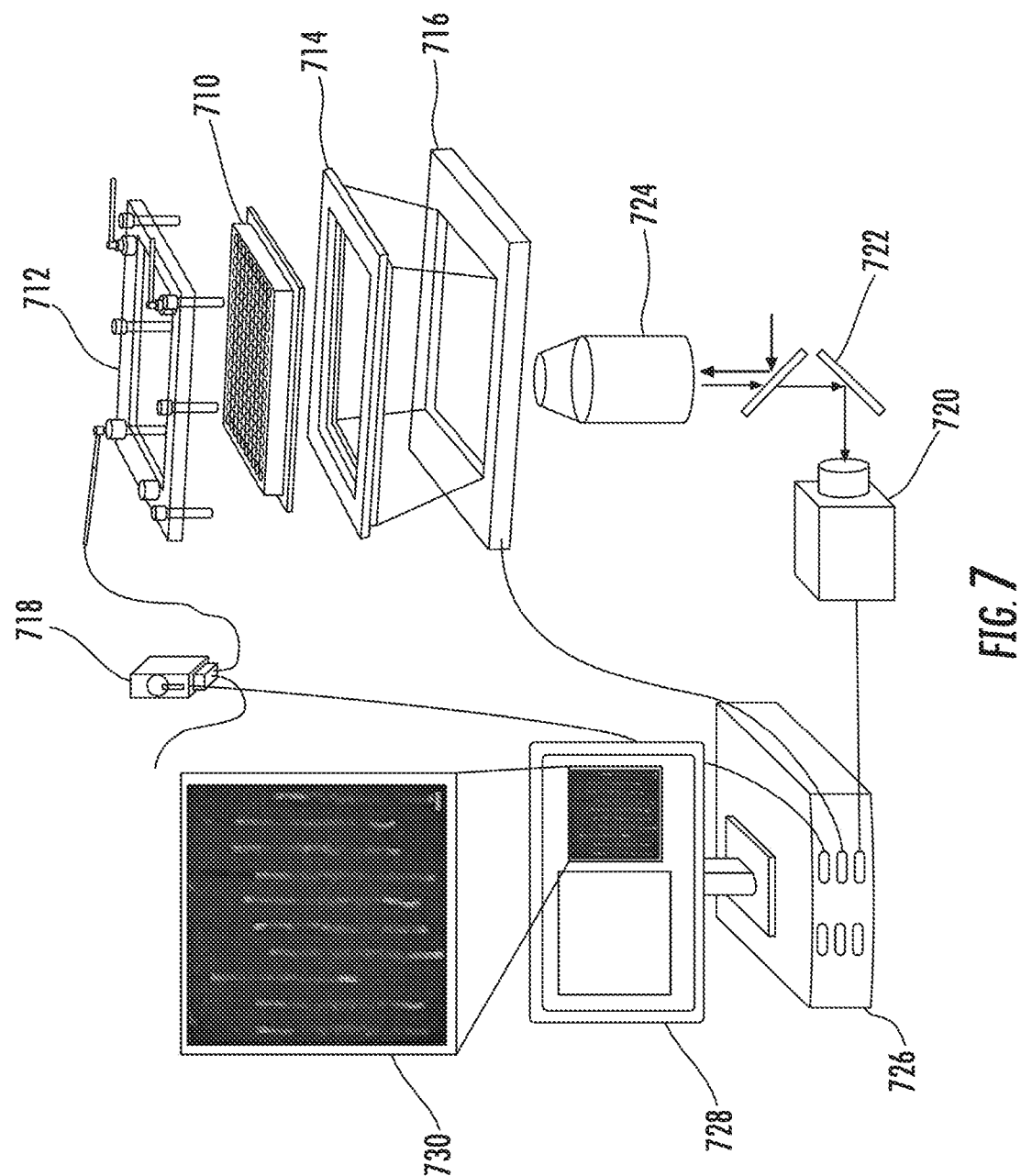
FIG. 7 is an example embodiment of an imaging system including a microfluidic device and a computer.

FIG. 7 is an example embodiment of an imaging system including a microfluidic device and a computer. The microfluidic device 710 is enclosed within an upper gasket 712 and a lower gasket 714. The device 710 and gaskets 712 and 714 may be operably connected to platform 716. Platform 716 may be a motorized platform that is controlled by a computer 726. The computer 726 also controls a valve 718 which can be used to influence the hydraulic pressure applied to device 710. FIG. 7 also shows a camera 720 used in conjunction with a mirror 722 and a objective 724. The computer 726 also includes a monitor 728 or other graphical user interface. The interface may be used to display results 730 of the imaging.

Example—Fabrication of the Microfluidic Device

The following description is merely one example of the fabrication of a microfluidic device. Microfluidic devices were fabricated using three-layer photo-lithography and single-layer soft-lithography techniques. In brief, we designed photo masks using AutoCAD 2013 and printed them on transparencies using 50K DPI resolution laser-plotter (Fineline Imaging). A 6 inch silicon wafer was spin coated with SU8-2025 photoresist (Microchem Corp.) at 2100 rotation per min (rpm) to obtain a height of ~45 µm (Layer-1, red). The layer was exposed to UV light using a photo-mask with the pattern for layer-1. The layer was developed and coated with the second layer of SU8-2025 at 1900 rpm for 33 sec to obtain a height of ~65 µm. The second layer was exposed to UV using a photo-mask with the pattern for layer-2. The layer was developed and coated with the third layer of Su8-2035 photoresist (Microchem Corp.) at 1650 rpm for 33 sec to obtain a height of ~85 µm. The third layer was exposed with a photo-mask with the pattern for layer-3. The SU8 mold with all three layers was treated with tridecafluoro-1,1,2,2-tetrahydrooctyl-1-trichlorosilane vapor (United Chemical Technologies) in a vacuum chamber at 40° C. to reduce surface adhesion during soft-lithography process.

Polydimethylsiloxane (PDMS, Dow Corning) was mixed in the ratio 10:1 and poured on the silanized SU8 mold with a 96-well PCR plate positioned on top of the SU8 features such that every well was aligned and placed on top of the circular pad at the entrance of every parallel immobilization design. The PCR plate was pre coated with silane vapor in vacuum chamber to ease its release after PDMS curing. An acrylic holder was placed on the silicon substrate with SU8 features to restrict outer dimension of the PDMS mold and achieve a height of around 8 mm of PDMS. PDMS layer was cured at 70° C. for 2 hours, peeled off from the SU8 mold, and released from the PCR plate. The PDMS block was punched for 12 exits and bottom of all 96 wells using a hydraulic punch (Syneo). The PDMS block was cleaned and bonded to a 3/16 inches borosilicate glass substrate using 100 W oxygen plasma. The device was finally cured at 70° C. for 6 hours for complete sealing.

Example—Gasket and Pressure System

The following description is merely one example relating to the subject matter discussed in this application. The gasket system comprised of an acrylic (Gasket-1) and an aluminum (Gasket-2) piece. An acrylic sheet of ¼ inches thickness was machined for gasket-1 with one buffer entry port and one air vent. A volume of 4.4 inches×3.0 inches×⅛ inches was milled out at the center of gasket-1 to hold sufficient buffer volume on top of all 96 wells embedded in the PDMS block. Two narrow lines were milled along the edge of larger sides of the rectangle to connect all 6 exit punches on each side of the PDMS block. Both exit channels in gasket-1 were connected to an external waste reservoir using a luer connector and fitted with a flexible tube. The size of gasket-2 was machined to match the flat-top motorized stage. Most of the material in gasket-2 was removed from central area to reduce material weight and enable fluorescence imaging from an inverted microscope. A thin step in gasket-2 matched the foot print of the glass substrate of PDMS devices. The top and the bottom gasket (gasket-1 and gasket-2) pieces were held tight using six screws to avoid buffer leakage during high pressure steps. The device was operated using filtered M9 from a 500 mL reservoir that was pressurized using compressed air. The pressure was transmitted to gasket-1 through a computer controlled solenoid valve.

Example—Automated Image Acquisition

The following description is merely one example relating to the subject matter discussed in this application. Bright field and fluorescent images were acquired using an Olympus IX73 microscope equipped with a 4 megapixel, 7.4 µm×7.4 µm pixel size, 15 frames per second maximum frame rates, CCD camera (MegaPlus ES4020, Princeton Instruments). Bright field and fluorescence images were acquired using a 2× (0.06 NA) and 10× (0.3 NA) objectives respectively using an in-house labVIEW program. The software controlled the movement of a motorized platform equipped with a 114 mm×75 mm (±44 nm resolution) flat-top XY translational stage, and a 500±0.002 µm traveling range piezo stage (MS2000, Applied Scientific Instrumentation). The scan area and translation commands were optimized for whole 96-well device design with 40 immobilization channels per well. In addition to the imaging routine for immobilization channels, the program detected alignment markers embedded on the PDMS block to quantify and compensate for offset values in all three axes during device imaging. The program integrated user defined parameters such as array size, number of image stacks, strain information in each well, and chemicals used in each well into the automated acquisition loop. Automated acquisition sub-routine acquired image stacks at every location and saved each frame by annotating them with an appropriate file name generated by the program. A full chip with 96-well device generated ~40 GB of images and stored them in the form of 16-bit images from the 4 megapixels CCD camera.

Example—Semi-Automated Image Analysis

The following description is merely one example relating to the subject matter discussed in this application. We developed an in-house graphical user interface (GUI) that allowed user to load saved image stacks at specific locations of the device from a specific screening experiment. All image stacks were loaded from a particular location of the chip and summed up to increase the contrast between the neurons and surrounding areas. The summed image was processed with a Gaussian low pass filter ($\sigma=1.0$) to attenuate high frequency features. The filtered image was projected on one side of the device and normalized to remove any background fluctuation due to non-uniform illumination. The algorithm searched for peaks above a threshold of $5\times10^4$ and separated by at least 150 pixels. Worms in a trap corresponded to large peak in the projection. An area of 2048 pixels×200 pixels centered at a peak was cropped to isolate single worms immobilized inside the microfluidic channel. Cropped worm image was thresholded so that 15% of pixels are above the threshold and converted to a binary image. A size filtering was used to remove all foreign particles smaller than 5000 pixels in area leaving only worm body in the field of view. Centroid of the worm body was either selected or predicted from the edge of the worm boundary. A smaller window of 201 pixels×201 pixels were selected around the worm centroid and analyzed for neuronal fluorescence. Assuming the brightest signal was from the neuron when it was in focus we searched for the brightest spot in the whole ROI through all the image stacks. The whole worm corresponding to the same focal plane was displayed to the user for scoring. In our C. elegans AD model study, VC4 and VC5 neurons were scored as 'Normal' or 'Degenerated' or 'Do Not Score' if they were 'healthy' or 'dim/missing' or 'not in focus' respectively. The whole worm was assigned with an additional remark for 'Dim Worm', 'Neurons Misshapen', and 'Axon Beading' if the worm was out of focus, VC4/VC5 cell bodies were misshapen, and neuronal process were beaded. Scoring options were displayed on the screen to be selected for each worm and the scores were saved in multi-dimensional array to be extracted for statistical analysis. The scores could be opened at later point for future references and review process along with the images.

Example—C. elegans Strain and Maintenance

The following description is merely one example relating to the subject matter discussed in this application. C. elegans were grown and maintained on nematode growth medium (NGM) agar plates with HB101 bacteria at 20° C. We used following C. elegans strains in this work: LX959 vsIs13 (lin-11::pes-10::GFP+lin-15 (+)), JPS67 vsIs38; unc-119; vsIs13; lin-15B, CZ1200 juIs76 (unc-25p::GFP+lin-15(+)), AM138 rmIs130 (unc-54p::Q24::YFP), AM140 rmIs132

(unc-54p::Q35::YFP). *C. elegans* strains LX959 and JPS67 were considered as wild type and APP mutant for neuronal degeneration studies in this work. In both strains all six VC neurons were marked with green fluorescent proteins (GFP) that can be visualized under fluorescent microscope. The AM138 and AM140 strains have 24 and 35 subunits of polyglutamine (PolyQ) labelled with YFP fluorescent protein in their body wall muscle cells.

*C. elegans* strains were maintained and synchronized at 20° C. for large population of liquid culture worms for high throughput studies in devices. Four healthy larval stage 4 (L4) hermaphrodite were transferred to a 10 cm diameter NGM plate containing HB101 bacterial lawn at 20° C. The plate would produce ~900-1000 gravid worms in 7 days which is then bleached to obtain 6000 viable eggs on bleaching. The bleached eggs were incubated at 20° C. in a 360 degree rotor for 24 hours for all the eggs to hatch and obtain age synchronized larval stage 1 (L1). Hatched L1s were cleaned by filtering hatched worms through a 20 µm filter that separated healthy L1s from unhatched eggs, unhealthy/dead L1s, and worm carcasses present in the liquid. Healthy L1s were collected in a glass tube and centrifuged at 1000 rpm for 2 min to achieve a worm density of ~100 worms/10 µL of liquid. A volume of 20 µL was dispensed in 32 wells of 24-well plates with an additional 1 mL of HB101 bacterial food in S. medium ($1\times10^9$ cells/mL). The worms were incubated at 20° C. and shook at 80 rotation per min (rpm) for 48 hours till they reach late L4 stage. Well plate was left on a horizontal surface for 10 min for the worms to sink down to the bottom of the well. 1 mL of freshly suspended HB101 was added in every well. 50 µL of FUdR (8.4 mM in water) was added to every well to avoid production of new young worms in the well volumes. Appropriate drug compounds were added in designated wells at known concentrations. The plates were incubated for 72 hours till the worm grew to day 3 adult (D3) stage. Each well of the 32 wells were dispensed to three wells on a 96 well plates with a 40 µm filter sieve. Worms were filtered, rinsed, and transferred to a fresh 96-well collection plate. Worms were pipetted from individual wells to the wells of a primed device to be used for imaging using high-throughput screening platform.

Example—Channel Geometry

The following description is merely one example relating to the subject matter discussed in this application. Total assay time is an important parameter and can be a bottle neck in high throughput studies. By reducing experimental time per run one can screen more number of compounds/populations that increases the possibility of finding new candidates in a chemical/genetic screen. We engineered a parallel architecture to immobilize a maximum of 3840 worms in a 96-well device with 40 channels per well to reduce the assay time for *C. elegans* screening platforms. The whole device is operated under a common gasket system and requires design optimization to achieve identical flow rates. The 96-well device is divided into smaller batches of 8-well sections connected together to common exit port. Both pairs of 6 exit ports ($E_1$ and $E_2$) on the two sides of the PDMS block align with the common exit grooves in the top-gasket on two sides. Worm entrances and exit channels are fabricated with largest thickness (85 µm) to avoid physical stress on worms inside the device during loading and reduce total hydraulic resistance. Worm motion gets reduced as they are pushed inside the device with multiple immobilization cycles and its relative position inside the device with lower channel widths of 65 µm (green) and 45 µm (red). The width of the channel is varied along the length to achieve aspect ratio (channel height to channel width) values within 1.2-0.4. Day 3 adult worms growing in liquid culture are immobilized in the region with ~1.0 aspect ratio. Every well is connected to the main flush outlet through an exit channel. A positive pressure gradient across the channel helps to load worms inside the channel and keep them in position during z-stack imaging.

Large dimension of the device demands special design layout and intelligent wiring of the exit channels to be able to achieve similar flow rates, faster loading, and identical worm immobilization within 40 traps of a well and amongst all 96 wells. Flow rates depend on the hydraulic resistances which is a function of the geometrical shape of the microfluidic channel. Since primary contributor to the hydraulic resistance is exit channel length, flow rate decreases with the relative position of the well with respect to the outlet punch. Device fabrication and operation requires minimum number of exit punches on the device boundaries out of the well region. We designed a symmetric 96-well device with two rows of 6 exits on top and bottom of the device. Each exit connects 2×4 wells with four different exit channel lengths. Well A01 situated on first row and closest to the exit presents minimum total hydraulic resistance and maximum flow rates. Flow rate reduces by ~50% for well D01 which is farthest from the exit. The variation in the flow rates are more prominent at higher well pressure. To reduce the effect of well location on flow rates hydraulic resistances are required to be modulated by compensating channel lengths with altered channel widths.

Example—Automated Image Acquisition

The following description is merely one example relating to the subject matter discussed in this application. In manual screening worms are mounted on agar pads and can be randomly positioned and oriented with respect to each other. This immobilization method requires additional amount of time and multiple field of views to screen every worm with high enough resolution. Labor intensive steps and long analysis time limit manual phenotypic screens to a few populations. Using our microfluidic immobilization device one can immobilize 4000 worms in parallel in a 96-well device format. Worms are loaded in 96-well device and clamped in between the gasket system before they are immobilized inside the trapping channels using an on/off pressure cycle. The device is mounted on a flat-top motorized XY stage and equipped with a 500 µm piezo. All 3-axis motions are controlled using an in-house labVIEW algorithm. The automation program has two main steps 1) worm immobilization, and 2) adaptive device scan with input parameters.

All 96 wells are filled with approximately 60 D3 adult worms in M9 buffer and clamped between the gasket systems to avoid pressure leakage during immobilization cycle. Top gasket is filled slowly with M9 buffer under 0.5 psi pressure and an open air vent. Slower filling rate avoids worm mixing between wells due to spill over during buffer flow. The air vent and both exits ($E_1$ and $E_2$) are closed immediately after the buffer is filled in the top gasket. Worms are able to swim freely at the well bottom and around the channel entrances. Worms are immobilized using an on-off cycle and under 4 psi pressure on the 96-well gasket system. Exits $E_1$ and $E_2$ are opened simultaneously on both sides to immobilize worms in all 96 wells simultaneously. The whole 96-well immobilization is achieved in less than 5 min and dispenses about 100 mL of buffer volume. One of the well from D01-E12 is viewed with low magnification (2×, 0.06 NA) to monitor extent of immobilization with cycle number. Once the immobilization cycle is complete the stage is manually moved to record XYZ coordinates of wells A01, A12, H01, and H12 using 10×, 0.3 NA objective to calibrate XY offset (θ) and XZ tilt (δxz and δyz) of the channel design with respect to the stage axes. The values are calculated for every position on the device and corrected for respective axes during imaging steps.

Example—Automated Image Analysis of *C. elegans* Disease Model

Figure 8A:
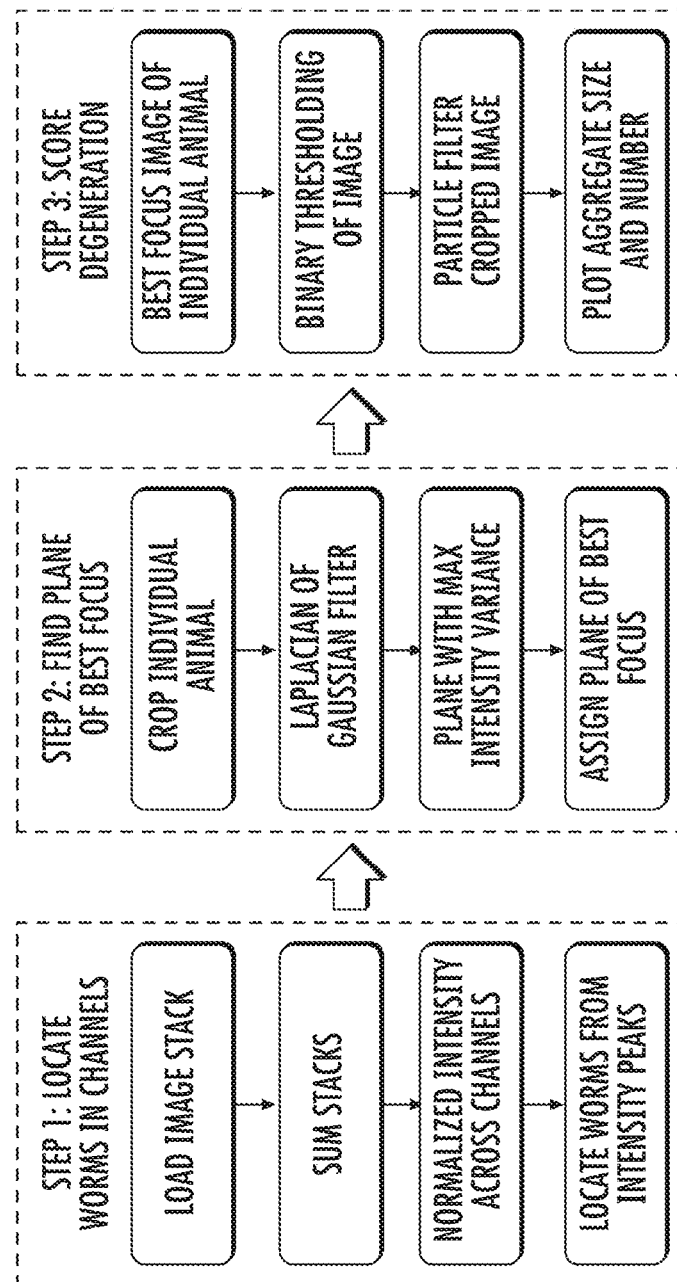
FIGS. 8A to 8H show automated image analysis to estimate the blob parameters using multiple z-stack images.
Figure 8B:
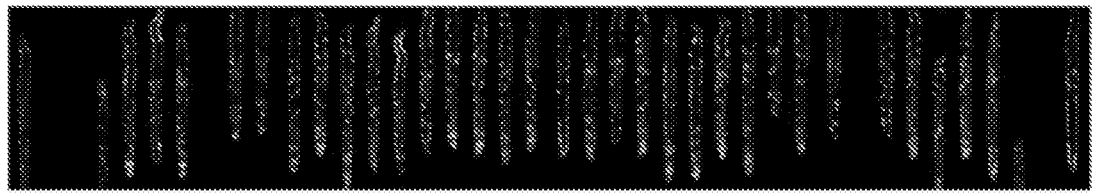
Figure 8C:
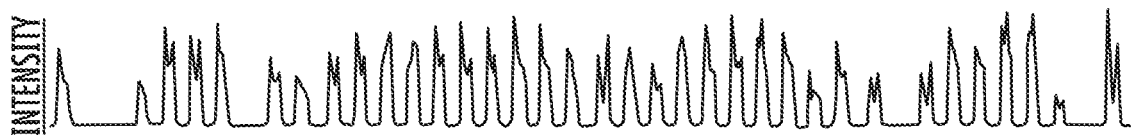
Figure 8D:
Figure 8E:
Figure 8F:
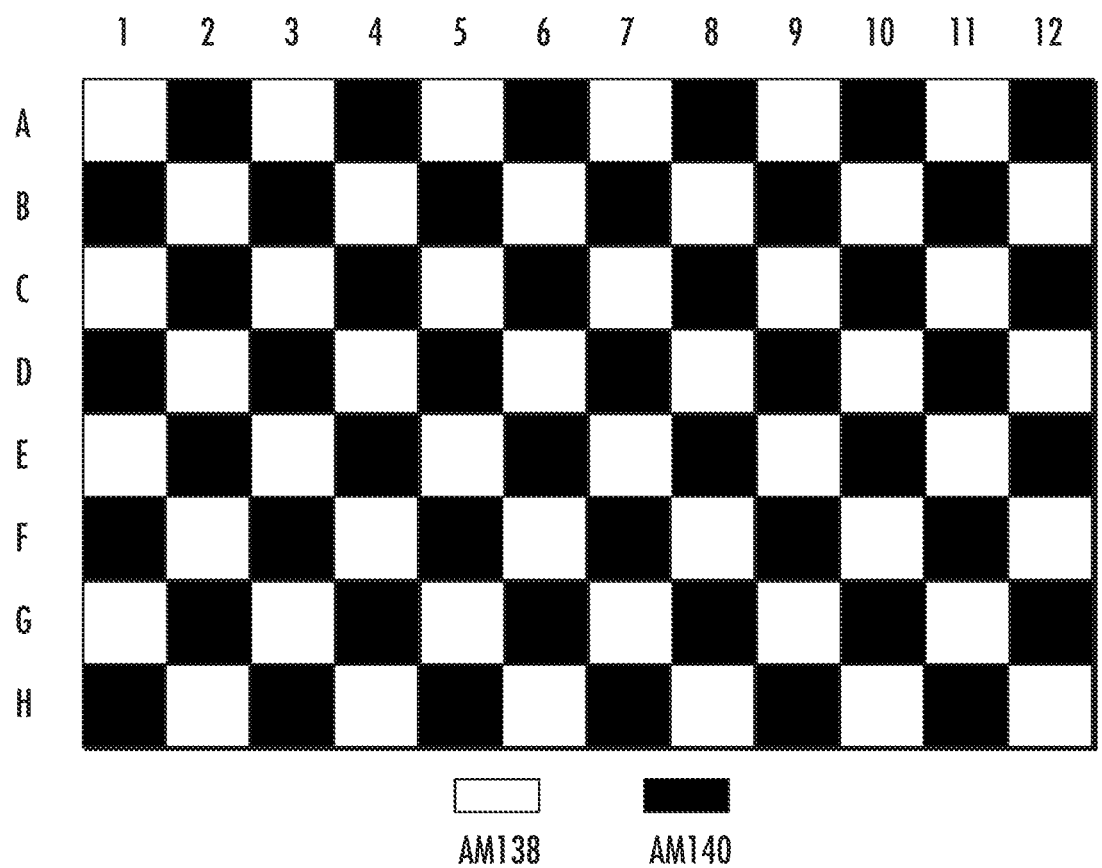
Figure 8G:
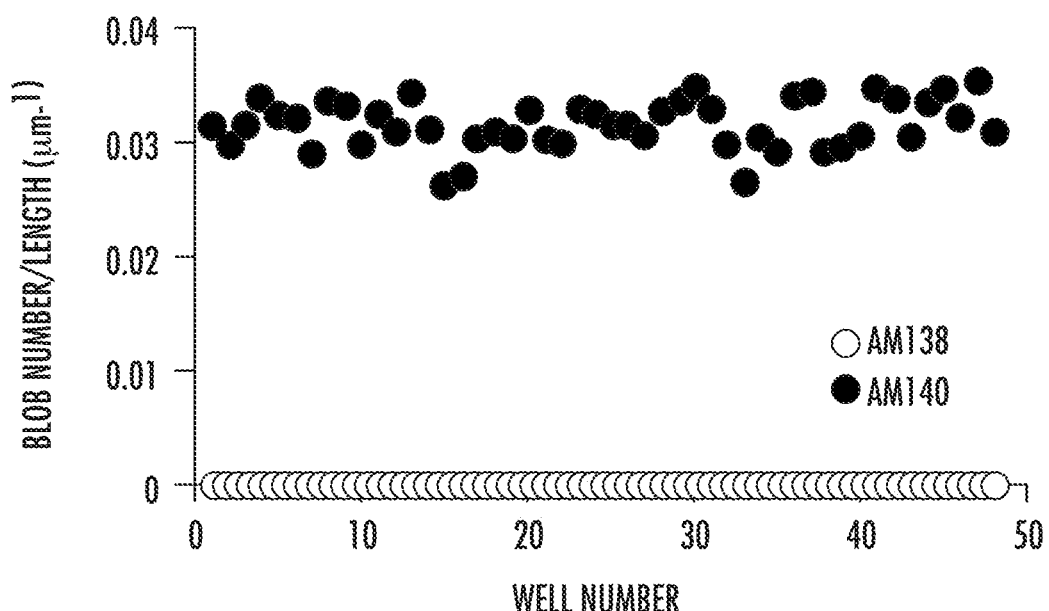
Figure 8H:
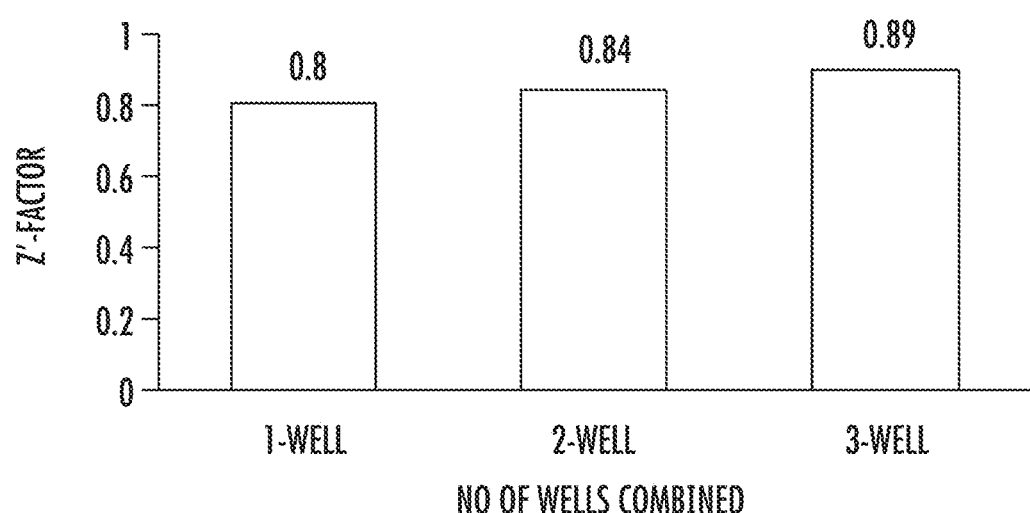

Manual image analysis of subtle phenotypical changes in such large-scale screens is another bottleneck that limits the overall speed of the assay. In order to demonstrate a full-automated data acquisition and analysis of high resolution fluorescence image stacks a protein aggregation disease model strain was used. The model, AM140 strain, has 35 ployQ chains in body wall muscles that shows age dependent aggregation. The control worms, AM138 strain, with shorter size of PolyQ fragments does not have such aggregation phenotypes at similar ages. To reduce the time required for image analysis and simplify the data handling process for large-scale, 3D stacks of images collected with this HTS system, a fully automated image analysis GUI was developed (FIG. 8A). The GUI aligns all four field-of-views and identifies channels with an immobilized animal corresponding to the peaks in the projected intensity profile (FIG. 8B, 8C). The algorithm extracts each animal at the best focus plane for image processing (FIG. 8D) and identifies the aggregates on the best-focal image for each animal (FIG. 8E). Phenotypical scores for each animal are saved automatically in a multi-dimensional array. Using this GUI, it was then possible to analyze all collected images from the whole 96-well chip for aggregation statistics of the trapped animals in approximately 15 min (FIG. 8F). This automated image analysis successfully reduced the data processing time by at least two orders of magnitude compared to all the automated steps of the GUI when performed manually. The phenotypical scores registered in the GUI for a whole 96-well experiment are exported into a scattered plot (FIG. 8G). Blob parameter shows a clear separation which yields a high Z'-factor of at least 0.80 for our screen platform with this model. Combining multiple wells can lower the variance leading to improved Z'-factor of the screen (FIG. 8H).

Example—384-Well Device for L4 Stage Animals

The following description is merely one example relating to the subject matter discussed in this application. We have designed and optimized a 384-well parallel immobilization device for super high-throughput immobilization and imaging of L4 stage *C. elegans*. In a similar fashion to the 96-well platform, each well leads to a microfluidic device. Each device is designed to orient and immobilize 30 L4 stage worms, for a total of 11,520 worms. Similar to the 96-well design, each set of 4×2 devices on one half of the platform are connected in series to an exit port. In order to optimize the resistances and achieve nearly equal flow rate, a staggered exit channel layout is designed. This staggered design connects 4×2 wells and overlaps with another 4×2 wells, creating roughly twice as many exit channels. Using this layout, the geometries of the exits arms have been optimized to achieve nearly identical aspect ratio and equal flow rates. This 384-well platform can be run with the same gasket setup as the 96-well platform. This system enable high-throughput optical interrogation of L4 stage *C. elegans* for large-scale imaging based studies that require large population sizes for phenotyping. Since the device interface is formatted for the standard 384-well platform, the technology can be a great value for commercial research labs and large scale high-throughput screening for *C. elegans*.

Example—Success of Exemplary Device

The following description is merely one example relating to the subject matter discussed in this application. A microfluidic based technology has been demonstrated that has single pressure input, no 3D valve control, 30 min pre-conditioning, parallel sample handling, adapted for multi-well plate handling, and an easy protocol for non-technologists. The device has twelve segments of 8-well platforms and can be fabricated as different sets of multiple of 8-well configurations. The device requires one ~5 psi pressure line and dispenses ~100 mL of buffer to run the whole chip with an appropriate gasket design. Users can select any rectangular size well array on the chip to scan predefined well numbers. All 96 wells with 40 immobilization channels per population immobilize maximum 3840 worms in less than 5 min. An on/off immobilization cycle pushes the worm inside a tapered channel geometry with varying aspect ratio, orienting ~4000 worms simultaneously in lateral direction. We captured all 40 channels per population in a whole 96-well device in less than 12 min using 10× objective (0.3 NA) and a large size camera. Worms immobilized inside the channel encounters higher level of stress causing increased autofluorescence thus reducing the sensitivity of the screen (poor signal to background ratio). We found similar level of background fluorescence in our microfluidic device. Hence, shorter immobilization and imaging time is very advantageous for *C. elegans* screens with weaker expression level of fluorescent reporters.

One full chip scan generates 4608 images from 3840 worms. The chip is capable for high resolution imaging screens with higher numerical aperture objectives and capture more z-stacks per location. A higher NA objectives with smaller field of view would require increase number of imaging locations to cover the whole length and all 40 channels. Since our immobilization cycle has nearly no head-tail orientation bias, one can capture all 40 channels with higher resolution and smaller field of view to acquire the signal from ~50% population with head or tail portion of the body. LabVIEW acquisition algorithm annotates data with all information and saves them in a folder. We developed a GUI to analyze fluorescence signals semi-automatically for neuronal phenotypes. The GUI loads all images from a user defined well population and displays single worm image stacks at a time to be inspected visually before scoring them for neuronal health. We scored all 3840 channels from a whole 96-well chip and saved them in a 9-dimensional array in approximately 8 hours. All the scores are pooled together from the multi-dimensional array and displayed for statistical tests. In an attempt to demonstrate the capability of the high-throughput system, we developed a fully automated image analysis for *C. elegans* Huntington's model with degenerating body wall muscles. The worms are imaged using similar image acquisition algorithm and can be analyzed for degeneration phenotype from the whole 96-well device in less than 15 min.

This screening platform can easily be adapted by a research laboratory for imaging based studies that require large population size phenotyping. Since the device interface is formatted for standard 96-well device, the technology can be a great value for commercial infrastructure for large scale high-throughput screening for *C. elegans*. An automated image processing algorithm that focuses on a specific neurodegenerative disease model may be able to analyze the complete data in less than 30 minutes. Even though we have used D3 stage *C. elegans* in our screen, one can use the same design principle for different stage of the worm with altered device dimension to achieve similar efficiency of immobilization. A younger stage worm would require smaller device dimension which can allow expansion of the 96-well format to larger well formats.

The subject matter described above may be carried out via a computer system for realization of a computer-implemented apparatus that may form all or a portion of one or more implementations or embodiments of the present disclosure. The computer system may include a computer, a keyboard, a mouse, and a display device (e.g., computer monitor) through which the computer may receive input/provide output, for example to a user, operator or another computer or system (not shown). Input/output devices such as the display device, keyboard, the mouse, and other means or mechanisms (e.g., touch screen interface) through which interaction with the computer system may occur are generally known in the art, and a detailed discussion thereof is omitted here for convenience only and should not be considered limiting. The computer includes a network port for connecting the computer to an internal or external network, such as, for example the network. The computer is connected to a storage device that includes program instructions for software application(s) that provides the logical functions of the computer-implemented apparatus and/or method(s) of the present disclosure. The storage device also contains a database for storing data.

Those skilled in the art will recognize that the program instructions for software applications implementing all or a portion of one or more embodiment(s) of the present disclosure may be written in a programming language such as Java or C++, and that the database may be implemented with a database package such as Microsoft Access™ database management system (DBMS) such as Microsoft SQL Server™, Microsoft SQL Server CE™, IBM DB2™, mySQL or postgreSQL.

The embodiments of the present disclosure may be implemented with any combination of hardware and software. If implemented as a computer-implemented apparatus, the present disclosure is implemented using means for performing all of the steps and functions described above.

The embodiments of the present disclosure can be included in an article of manufacture (e.g., one or more computer program products) having, for instance, computer useable or computer readable media. The media has embodied therein, for instance, computer readable program code means, including computer-executable instructions, for providing and facilitating the mechanisms of the embodiments of the present disclosure. The article of manufacture can be included as part of a computer system or sold separately.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of the present disclosure is not limited to the particular examples and implementations disclosed herein, but is intended to cover modifications within the spirit and scope thereof as defined by the appended claims and any and all equivalents thereof.

What is claimed is:

1. A microfluidic device comprising:
two or more substrates bonded together to form a plurality of trapping devices, each trapping device comprising:
a sample reservoir;
an inlet channel in fluid communication with the sample reservoir;
a plurality of trapping channels in fluid communication with the inlet channel, each trapping channel having a length, a width, and a height; and
an exit channel in fluid communication with the plurality of trapping channels, wherein:
the length of each trapping channel is measured in a direction from the inlet channel to the exit channel through the trapping channel, the width is measured in a direction orthogonal to the length direction and within a plane that is parallel to the surface of at least one of the substrates, and the height is measured in a direction that is orthogonal to the length and width directions,
each trapping channel comprises a plurality of sections arranged end to end along the length of the respective trapping channel, wherein the widths of at least two adjacent sections vary with respect to each other,
for at least one trapping channel, the heights of at least two of the plurality of sections for trapping a biological subject differ from each other such that the aspect ratio of the width to the height of the respective section is within a range of about 0.2 to about 2.0, and
the exit channels of at least two of the plurality of trapping devices are in fluid communication with one another via an intermediate exit channel.

2. The microfluidic device of claim 1, wherein the plurality of sections includes a first section, a second section, and a third section, wherein the first section of the trapping channel is proximate to the inlet channel, the third section of the trapping channel is distal to the inlet channel, and the second section is positioned between the first and third sections; and wherein the height of the first section is greater than the height of the second section, and wherein the height of the second section is greater than the height of the third section.

3. The microfluidic device of claim 1, wherein the widths of the at least two adjacent sections that vary in widths, and/or the heights of the at least two sections that differ in height change gradually.

4. The microfluidic device of claim 1, wherein a plurality of intermediate exit channels joins in fluid communication with a final exit channel.

5. The microfluidic device of claim 1, wherein the respective exit channels of the at least two trapping devices are sized such that a flow through each exit channel experiences similar hydraulic resistance.

6. The microfluidic device of claim 1, wherein each trapping device further comprises a micro-well having a substantially frustoconical shape, wherein the micro-well is in fluid communication with the sample reservoir such that biological subjects and reagents in the well are able to be deposited into the sample reservoir.

7. The microfluidic device of claim 1, wherein a first end of the inlet channel adjacent the reservoir has a height of between about 1 µm and about 500 µm and a width of between about 1 μm and about 750 μm, wherein the inlet channel connects the plurality of the trapping channels.

8. The microfluidic device of claim 7, wherein the length of each of the plurality of trapping channels is between about 200 μm and about 6 mm.

9. The microfluidic device of claim 1, wherein the geometry of each trapping channel is configured to position a single biological subject in a specific orientation.

10. The microfluidic device of claim 9, wherein the biological subject comprises a *C. elegans* worm.

* * * * *